US012484823B1

(12) United States Patent
Erney

(10) Patent No.: US 12,484,823 B1
(45) Date of Patent: Dec. 2, 2025

(54) APPARATUS AND METHOD FOR PREPARING A PATIENT'S SCALP FOR ATTACHING ELECTRODES

(71) Applicant: Lorraine M. Erney, Emmaus, PA (US)

(72) Inventor: Lorraine M. Erney, Emmaus, PA (US)

( * ) Notice: Subject to any disclaimer, the term of this patent is extended or adjusted under 35 U.S.C. 154(b) by 925 days.

(21) Appl. No.: 17/507,794

(22) Filed: Oct. 21, 2021

Related U.S. Application Data

(63) Continuation-in-part of application No. 16/045,012, filed on Jul. 25, 2018, now abandoned.

(51) Int. Cl.
*A61B 5/251* (2021.01)
*A61B 5/291* (2021.01)

(52) U.S. Cl.
CPC .............. *A61B 5/251* (2021.01); *A61B 5/291* (2021.01); *A61B 2562/0209* (2013.01)

(58) Field of Classification Search
CPC . A61B 2562/14; A61B 90/80; A61B 5/04025; A61B 5/04026; A61B 5/291; A61B 5/259; A61B 5/325
See application file for complete search history.

(56) References Cited

U.S. PATENT DOCUMENTS

| | | | | |
|---|---|---|---|---|
| 7,614,811 | B2 * | 11/2009 | Kaufman | A61M 35/006 401/133 |
| 7,637,401 | B2 * | 12/2009 | Py | B65D 35/06 222/107 |
| 2002/0019588 | A1 * | 2/2002 | Marro | A61B 5/291 600/383 |
| 2007/0004978 | A1 * | 1/2007 | Ponton | A61B 5/6814 600/397 |
| 2018/0229019 | A1 * | 8/2018 | Lareau | A61M 39/26 |
| 2019/0365270 | A1 * | 12/2019 | Bachelder | A61B 5/282 |

* cited by examiner

*Primary Examiner* — Adam Z Minchella
(74) *Attorney, Agent, or Firm* — Wilkinson Law Office; Clinton H. Wilkinson

(57) ABSTRACT

An apparatus and method for preparing the skin of a patient's scalp for attaching electrodes, the method comprising the steps of providing a squeezable member having a hollow interior, wherein a skin abrasive solution is in the interior, wherein the squeezable member includes a restrictive member having a restrictive opening for restricting flow of the skin abrasive solution out of the squeezable member, and an applicator tip through which the solution leaving the restrictive member exits the squeezable member including an interior member and a compressible exterior member having corresponding shapes; squeezing the squeezable member; scrubbing skin portions of the scalp of the patient with the tip; and attaching electrodes to the skin portions of the patient's scalp.

18 Claims, 6 Drawing Sheets

APPARATUS AND METHOD FOR PREPARING A PATIENT'S SCALP FOR ATTACHING ELECTRODES

FIELD OF THE INVENTION

The present application relates to electrodes, and more specifically to the attachment of electrodes to a patient. In particular, a method and apparatus are described for preparing the skin on a patient's scalp for attachment of electrodes. such as for performing an electroencephalogram.

BACKGROUND OF THE INVENTION

Electroencephalography, or EEG, is a method of recording electrical activity in the brain. In particular, EEG measures voltage fluctuations resulting from ionic current within the neurons of the brain. Typically, an EEG is performed by attaching electrodes to the patient's scalp (the anatomical area bordered by the face in the front, and by the neck at the sides and hack). Once attached, it is possible to measure voltage fluctuations over time.

EEG has been used for various forms of medical diagnosis including epilepsy. For purposes of studying brain function, EEG has several advantages over other techniques. For example. costs may be lower, equipment is significantly less bulky than other types of equipment, temporal resolution is very high, subject movement may not affect results, the test is silent, claustrophobia is not an issue, high-intensity magnetic fields are not required, radioactivity is not required, and testing is fairly noninvasive.

Performance of an EEG comprises the following steps: supplying electrodes; preparing the scalp for electrode placement (often using a form of light abrasion to reduce impedance); and placing the electrodes on the scalp using a conductive paste or gel. Each step will now be described separately.

Electrodes are supplied with each attached to an individual wire. The electrodes a are supplied in the form of cups that are available in different metals. Silver/silver chloride or gold cup electrodes may desirably be used due to their recording properties. These materials are desirable because they have low impedance.

In one example of the prior art, the head is measured according to the international 10/20 system of electrode placement. Electrode placement locations can then be marked using a grease pencil. Instructions for measuring the head based on the international 10/20 system of electrode placement are known to one of ordinary skill the art and will not be repeated here.

Prior to attaching the cups to a patient's scalp, the skin must be prepared. An abrasive solution may be used to lower impedance of the electrode connection. Thus. an abrasive prep (hereafter "prep") is used to clean the area where the electrode will be applied. The objective is to remove oils and dried skin from the location where the electrodes will be attached. In addition, a slight abrasion of the skin allows for low impedance. Various solutions are commercially available for performing abrasive prep and are sold under various trade names including NUPREP, LEMON PREP, and SKIN PURE. Typically, a cotton tipped applicator is used to apply a small amount of prep to the location where each electrode placement location has been marked. Such a cotton tipped applicator may be or resemble a cotton tipped swab sold under the trade name QTIP. Such swabs (as described by Wikipedia) include one or two small wad(s) of cotton wrapped around one or both end(s) of a short rod made of wood, rolled paper or plastic. Using the cotton tipped applicator, prep may be wiped several times in one direction over that spot. The goal of this procedure is to remove dead skin cells and oils and to slightly abrade the skin.

Next, each electrode cup is filled with conductive paste. Conductive paste allows each cup to be adhered to the scalp. The conductive paste also ensures that the contact impedance of the electrode-skin interface is reduced. Examples of conductive paste are sold under several trade names including TEN20 and ELEFIX. Each cup is then pressed onto each location that was prepared with the prep using downward pressure. The electrodes may then be covered with gauze or cotton. Frontal electrodes may be secured using medical tape. Sometimes, the electrode wires are secured together in order to reduce or eliminate artifacts from the recording.

Each electrode is then plugged into the EEG machine. By doing so, each electrode is connected to an input of a differential amplifier in order to amplify the voltage being measured.

The voltages are subsequently recorded. Sometimes "activation" procedures may be used including strobe lights, eye closure, mental activity, hyperventilation, etc. Each EEG signal can then be stored and filtered for display.

SUMMARY OF THE INVENTION

A method of attaching electrodes to a patient, the method comprises the steps of providing a squeezable member having a hollow interior, wherein a skin abrasive solution is in the interior, wherein the squeezable member includes a restrictive member having a restrictive opening for restricting flow of the skin abrasive solution out of the squeezable member, and a tip through which the solution leaving the restrictive member exits the squeezable member; squeezing the squeezable member; scrubbing skin portions of the scalp of the patient with the tip; and attaching electrodes to the skin portions of the patient's scalp.

DETAILED DESCRIPTION

Figure 1:
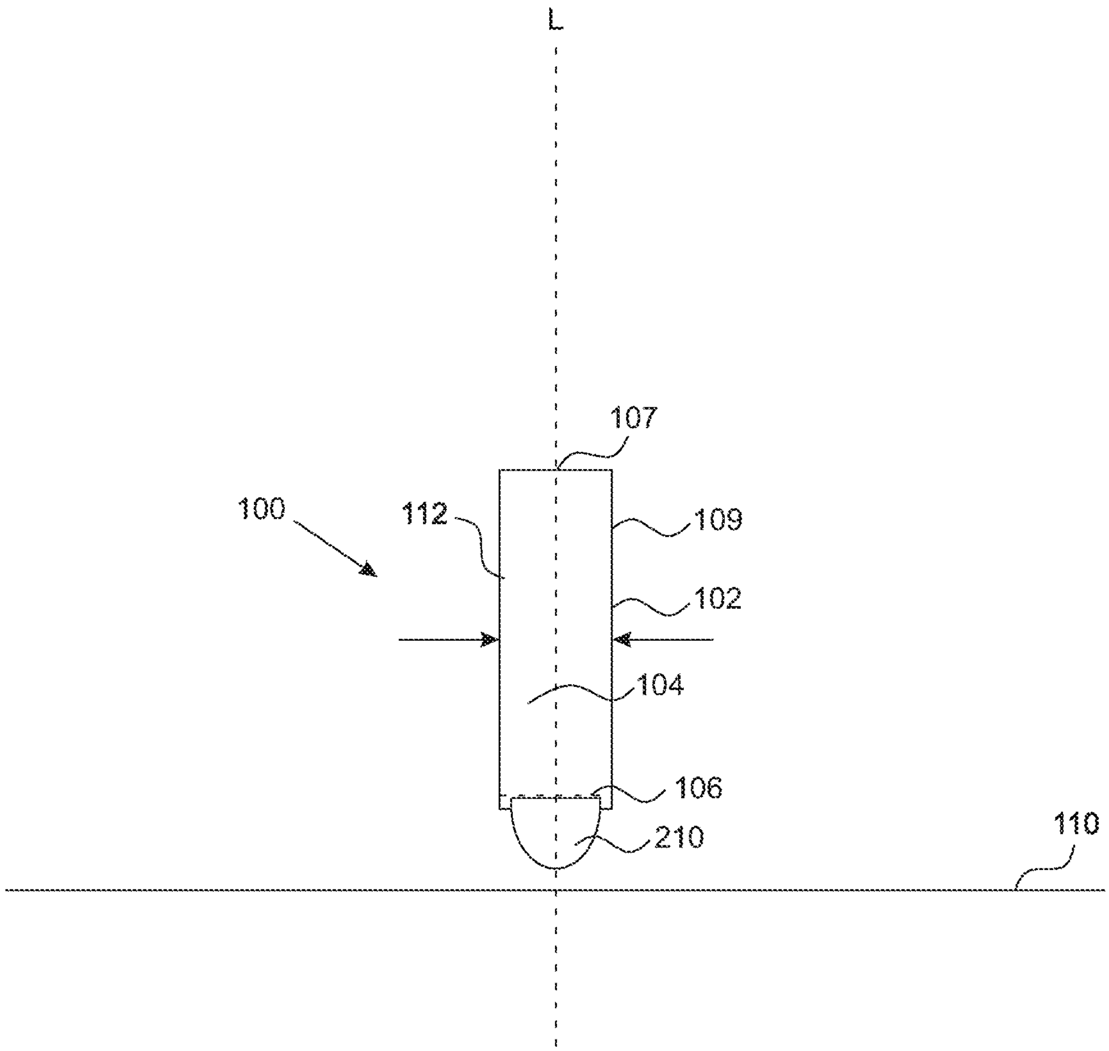
FIG. 1 is a side view of a squeezable member applying prep solution to skin in accordance with an exemplary embodiment of the present invention.

The prior art method of applying prep has several problems which makes the process undesirable. As previously explained, prep is applied to a patient's scalp through the use of a cotton tipped applicator or swab. The cotton tipped applicator is dipped into a container of prep, and then the cotton tipped applicator is rubbed on locations on the patient's scalp.

As the prep goes from location to location on the patient's scalp, it is desirable to keep the cotton tipped applicator saturated with prep. Thus, the technician applying the prep repeatedly moves his/her hand back and forth: dipping the applicator into a solution of prep and then rubbing the applicator on the patient's scalp in various locations.

There are problems with this procedure, namely the time needed to apply the prep and the possibility of applicator breakage.

Because the technician is moving the applicator hack and forth between the solution of prep and the patient's head, time is lost in the process of moving between the patient's head and the solution of prep. This can be particularly inconvenient for a patient. For example, if a patient is a child, or the patient is an adult with a disability such as a learning disability, the patient might be impatient or potentially frightened by the process of being prepared for an EEG recording. In one example, the patient may have difficulty sitting still. In another example, if the patient is very upset, the patient can start to cry, and/or can be very agitated with the result of frequent head movements. With any type of head movement, application of prep onto a patient's head can become very challenging. Thus, a technician will attempt to apply prep on a patient's head as quickly as possible. If the technician is continuously moving his/her hand back and forth between the patient's head and a solution of prep, this process of hand movement increases the amount of time needed to apply prep to all the locations on a patient's head, and/or creates unnecessary delays between applying prep to each location on the patient's head.

Breakage of the applicator is another concern. An applicator may be comprised of wood (as opposed to other materials) because of low cost as well as sufficient structural strength. In other words, the cotton tipped applicator needs to be sufficiently strong so that a technician can apply pressure on to the patient's head while grasping the applicator. This pressure may be needed in order to slightly abrade the skin in order to lower the impedance of the electrode connection. Unfortunately, if a technician applies too much pressure, then the applicator might break, with the result that a sharp point is formed, and that is possibly pointing towards the patient's head. Even if a technician is "perfect" in the amount of pressure being applied, if the patient suddenly jerks his/her head in the wrong direction, and with sufficient force, the jerking motion may result in the applicator snapping in half. Again, this may result in a dangerous situation where a technician is left holding only a portion of the applicator, with a sharp end facing towards the patient's head.

Accordingly, in an exemplary embodiment of the present invention, squeezable member 100 is provided as shown in FIG. 1. Squeezable member 100 allows prep to be applied to skin layer 110 (on a patient's scalp) and also permits skin layer 110 to be cleaned and slightly abraded. FIG. 1 is a side view that illustrates some exemplary embodiments of the present invention, and some details may be obscured for purposes of providing an overview of the present invention. Squeezable member 100 includes body 102. Body 102 includes a hollow interior 104 in which prep solution either is located, or is introduced. Thus body 102 is basically a container that is shown in an inverted position. Body 102 includes bottom 107 and sidewalls 109. Thus body 102 in one embodiment extends along elongated longitudinal axis L. In one embodiment, body 102 is cylindrical, although this is merely exemplary. Body 102 can be molded in various shapes including elliptical, rectangular. cylindrical. or other cross-sectional shapes. In one embodiment, body 102 is formed as an integral one-piece structure by an injection molding process. In another embodiment, body 102 is formed by bonding together two separate pieces that are formed by injection molding. In a further example, body 102 is formed by a blow-molding process. These manufacturing processes are merely exemplary. The volume within hollow interior 104 can vary depending on the desired volume capacity.

In operation, squeezable member 100 is provided. Also, squeezable member 100 may be provided with abrasive prep in hollow interior 104. In another embodiment, squeezable member 100 is provided empty and is then filled with abrasive prep. Abrasive prep is sold under several brand names such as NUPREP, LEMON PREP, and SKIN PURSE. Squeezable member 100 may be inverted into the position shown in FIG. 1. In one embodiment, gravity enables abrasive prep within hollow interior 104 to flow through applicator 210 and onto skin layer 110. In another exemplary embodiment, the step of squeezing body 102 assists in forcing abrasive prep out of body 102, through tip of applicator 210 and onto skin layer 110.

In one embodiment, sidewalls 109 of body 102 are flexible. This flexibility enables body 102 to be squeezed from opposite sides as shown by the exemplary and illustrative opposing arrows that are illustrated in FIG. 1. The ability of body 102 to receive squeezing pressure from opposite directions (as shown, for example, by the illustrated opposing arrows) enables the volume of hollow interior 104 to be reduced, thus allowing the contents of body 102 to flow out of an opening therein. The location at which squeezing pressure is shown is merely exemplary.

Squeezable member 100 includes applicator 210. Applicator 210 may include a tip that includes materials to provide comfort to a patient when applicator 210 is in contact with skin layer 110. Thus, applicator 210 may be comprised of a sponge-like material. Alternatively, the tip of applicator 210 may have a hard interior and an exterior softer than the hard interior. Exemplary exterior is formed of textiles or fabrics. Details regarding applicator 210 are described below.

Squeezable member 100 may also include optional restrictive member 106. Restrictive member 106 may provide some form of restriction as liquid within hollow interior 104 flows through applicator 210 and onto skin layer 110. Details regarding restrictive member 106 are also provided below.

As a result of gravity, and/or squeezing of body 102, prep is now introduced onto skin layer 110. Using for example a back-and-forth motion, applicator 210 may be rubbed on skin layer 110 in order to clean skin layer 110 with the abrasive prep that has come out of body 102. In one embodiment, the actions of 1) allowing abrasive prep to flow out of body 102 and 2) rubbing applicator 210 on skin layer 110, occur concurrently. In another exemplary embodiment, flow of abrasive prep out of body 102 and rubbing of skin layer 110 by applicator 210 occur sequentially (i.e., allow abrasive prep to flow out of body 102, subsequently rub skin layer 110 with applicator 210, repeat). Alternatively, a combination of the above steps may occur in which rubbing of skin layer 110 and exiting of abrasive prep from body 102 first occurs simultaneously, then occurs sequentially, etc. The hard interior enables sufficient force to be applied against the skin surface by the softer exterior for the abrasive prep to easily clean the skin layer 110.

In one exemplary embodiment, squeezable member 100 is supplied in a closed container and filled with abrasive prep prior to being received for patient use. In this exemplary embodiment, the technician removes squeezable member 100 from packaging, preps a patient head for EEG recording, and when done simply disposes of squeezable member 100. In another exemplary embodiment, squeezable member 100 is refillable, and applicator 210 is replaceable. Thus, for example, prior to use, squeezable member 100 is provided empty, squeezable member 100 is filled with abrasive prep, applicator 210 is rubbed on a patient's skin layer 110 while abrasive prep is concurrently and/or sequentially exiting squeezable member 100, and after patient preparation is complete, applicator 210 is discarded or sterilized. Squeezable member 100 is then refilled with abrasive prep, and either applicator 210 is attached to body 102 prior to further patient use, or a previously-used applicator is sterilized and subsequently attached to body 102. Several exemplary embodiments will now be provided in order to illustrate both methods of operation.

Figure 2:
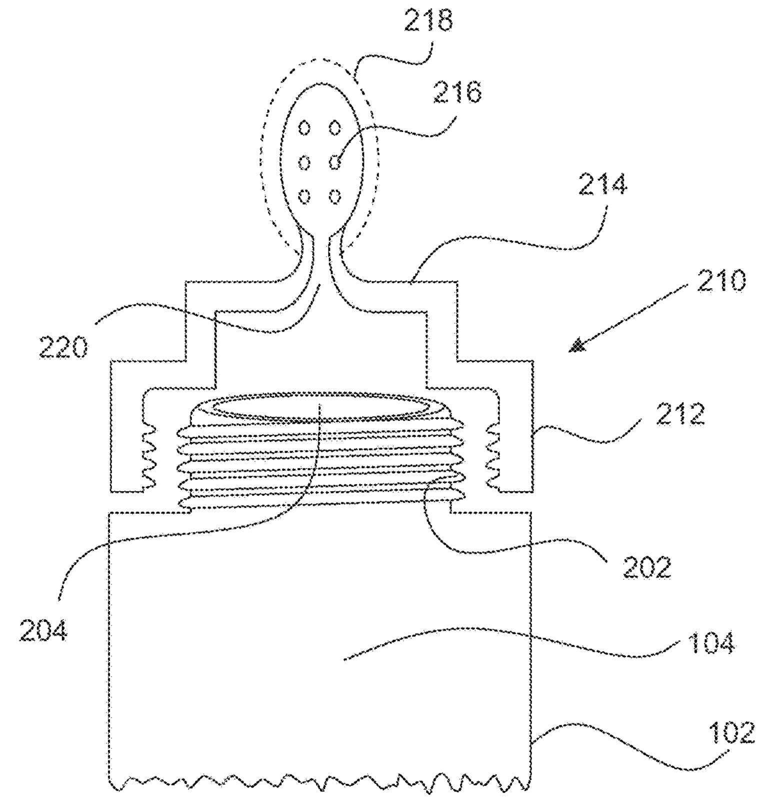
FIG. 2 is a side view of a removable tip and retainer that is part of a squeezable member in accordance with an exemplary embodiment of the present invention.

FIG. 2 illustrates an exemplary embodiment of the present invention in which one configuration is illustrated for applicator 210. In the exemplary embodiment shown in FIG. 2, applicator 210 and body 102 are two separate pieces, although this is merely exemplary. In other words, applicator 210 and body 102 may be implemented as a single integral piece, and this is described further below.

In the embodiment shown in FIG. 2, applicator 210 is comprised of tip 216 and retainer 212. In one embodiment, tip 216 is rounded, but this is merely exemplary. Retainer 212 is attached to the neck 202. The attachment between retainer 212 and neck 202 may be in several different ways. The structure shown in FIG. 2 entails attaching retainer 212 to the neck 202 using the threaded screw configuration. In addition, a male-female configuration shown in FIG. 2 may be replaced with a female/male configuration. Furthermore, while a threaded configuration is shown, other configurations are possible including a friction hold and/or a tongue and groove hold.

Tip 216 may be oval-shaped as shown in the figure, although this is merely exemplary. Tip 260 may be manufactured using various exemplary manufacturing processes including injection molding and blow molding. Tip 216 as shown in FIG. 2 includes an interior member having a hollow interior and a plurality of small sized openings from which abrasive prep exits tip 216. Furthermore, the interior member of tip 216 is covered with a soft (or compressible) exterior member 218 in order to reduce friction between tip 216 and skin layer 110. An exemplary layer may be cotton, although other fibers are also contemplated including polyester type fibers. The interior member of tip 216 is more rigid than exterior member 218. In addition, the shape of exterior member 218 in some embodiments is similar or corresponds to the shape of the interior member, which assists a technician in applying pressure on to the patient's head while grasping the applicator and contacting the tip 216 with the patient's head with any part of the exterior surface and at any angle with good scrubbing results. The corresponding shapes of the more rigid interior member and less rigid exterior member of the tip provide a soft contact surface with the skin as well as the rigidity required for the technician to apply adequate manual pressure against the skin surface with the tip as the angle of the tip continually changes due to the back and forth rubbing motion of the tip against the skin. This greatly improves the efficiency of the skin cleaning process using the applicator, while also improving patient safety since the tip 216 is formed of materials that will not break as a result of manual forces exerted on the applicator during skin cleaning. Tip 216 is mounted to a base that includes restrictive member 214. Restrictive member 214 includes restrictive opening 220 through which abrasive prep flows. Restrictive opening 220 may have a diameter which is smaller (or much smaller) t the diameter of tip 216. The small diameter of restrictive opening 220 restricts the rate at which abrasive prep flows into tip 216 and towards skin layer 110. Because the diameter of restrictive opening 220 is smaller than the diameter of tip 216, this feature may need to be addressed during the manufacturing process. Thus, for example, after tip 216 is manufactured using injection molding, it may be desirable to manufacture applicator 210 as identical bisymmetrical halves that arc bonded (or fused) together during the manufacturing process.

As previously explained, applicator 210 is attached to body 102 using various methods that include and are not limited to a threaded attachment, a friction attachment, a tongue and groove attachment, etc. Also, in another exemplary embodiment, applicator 210 and body 102 are manufactured so that applicator 210 and body 102 are integrated into a single piece. As previously explained, if injection molding is used as the form of manufacturing, it may be desirable to form squeezable member 100 in two separate identical bisymmetrical pieces that are bonded/fused together during the manufacturing process.

Body 102 includes body opening 204. When squeezable member 100 is inverted, abrasive prep flows out of hollow interior 104, through body opening 204, through restrictive opening 220, into tip 216, and through cover 218 before coating skin layer 110.

Prior to performing an EEG on a patient, squeezable member 100 is supplied having body 102 with hollow interior 104. Abrasive prep (a skin abrasive solution) may either be included in the hollow interior 104 or added to hollow interior 104 prior to use. Squeezable member 100 includes applicator 210 having tip 216 (at the end of applicator 210) through which the prep exits squeezable member 100. The squeezable member includes a restrictive member, either in body 102 or applicator 210. In the example shown in FIG. 2, squeezable member 100 includes restrictive opening 220 for restricting flow of prep out of tip 216 of squeezable member 100. In the example shown in FIG. 2, restrictive opening 220 is smaller than a cross-sectional area of hollow interior 104. In the example shown in FIG. 2, applicator 210 includes retainer 212 and tip 216. In another example, restrictive opening 220 is smaller than width of tip 108.

Squeezable member 100 may be squeezed to assist in the flow of prep out of squeezable member 100.

As (or after) prep flows onto the patient's scalp, skin portions of the patient's scalp are scrubbed with tip 216. Scrubbing may be accompanied by pressure against the patient's scalp. In one embodiment-pressure is applied to the scalp in a direction orthogonal to the direction in which squeezable member 100 is squeezed. In another embodiment, squeezable member 100 is used to apply pressure at an angle that is not exactly orthogonal to the patient's scalp, but the pressure has an orthogonal pressure vector component.

Electrodes are then attached to the patient's scalp at the locations where the patient's scalp was scrubbed.

During use, if prep is not already in hollow interior 104, then prep is added to hollow interior 104. Adding prep to hollow interior 104 may be performed as follows: Applicator 210 may be unfastened from body 102, prep is poured into hollow interior 104, and applicator 210 may be reattached to body 102. Applicator 210 that is reattached to body 102 is either an applicator 210 that was previously detached from body 102 or a new applicator 210.

Squeezable member 100 may thus be provided as a kit, with body 102 and a plurality of applicators 210. In this manner, each applicator 210 that is used may be discarded and replaced with a new (and clean and/or sterile) applicator 210.

The above explanation is with regard to the embodiment shown in FIG. 2, but may also apply to other embodiments of the present invention as further described below.

Figure 3:
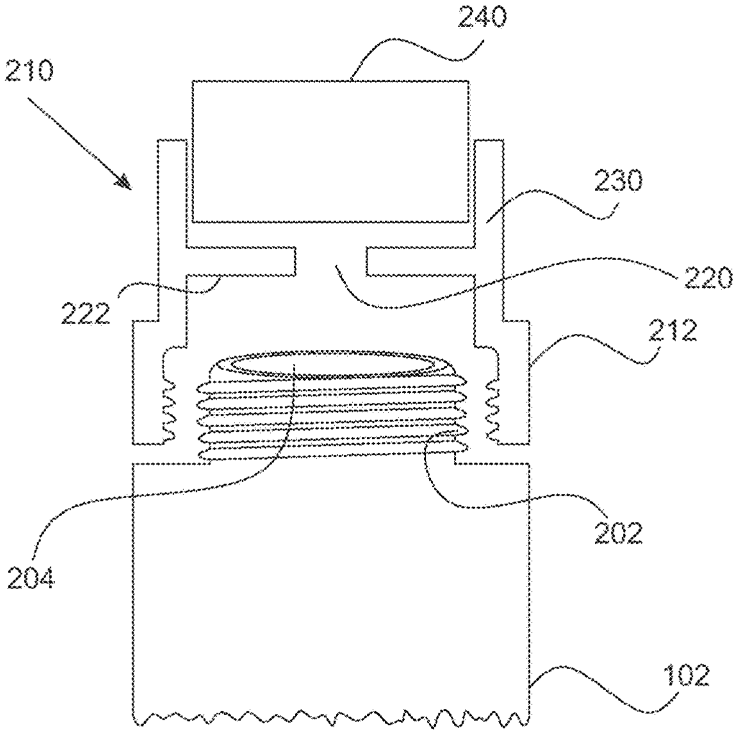
FIG. 3 is a side view of a further removable tip and retainer that is part of a squeezable member in accordance with a further exemplary embodiment of the present invention.

FIG. 3 illustrates a further exemplary embodiment of the present invention. In FIG. 3, tip 216 has been replaced with compressible tip 240. Compressible tip 240 may be a sponge-like material. Compressible tip 240 may be comprised of a material such as polyester, polyurethane, or vegetal cellulose. Compressible tip 240 may have a variety of different shapes and sizes and amounts of compressibility. As shown in FIG. 3, the protruding end of compressible tip 240 may be flat, and may be perpendicular to its sidewalls, although this is merely exemplary. Thus, for example, the protruding end of compressible tip 240 may be angled so that when squeezable member 100 is inverted, it may comfortably be held at an angle relative to skin layer 110 in order to improve holding comfort of squeezable member 100. Alternatively, compressible tip 240 may have a rounded protruding end.

Compressible tip 240 sits within applicator 210 and rests on restrictive member 222. Restrictive member 222 may be one of a plurality of restrictive members 222 that extend inwardly from the inner walls of applicator 210. While restrictive member 222 extends inwardly from the inner walls of applicator 210, the location of one restrictive member 222 relative to another may result in spaces therebetween, thus allowing abrasive prep to flow to those spaces. Alternatively, restrictive member 222 can be another shape such as a disk with a central opening. The disk may be adhered to the interior of applicator 222. Adhering of restrictive member 222 within applicator 210 may be via chemical bonding, bonding during the manufacturing process, or a tongue and groove configuration. Compressible tip 240 may be held in place within applicator 210 with a friction hold, adhesive, and/or it may rest on restrictive member 222. Applicator 210 includes sidewalls 230 in which compressible tip 240 is inserted.

During actual operation, abrasive prep flows through body opening 204 of body 102, through restrictive opening 220, through compressible tip 240 and onto skin layer 110. Furthermore, while FIG. 3 shows retainer 212 and body 102 as two separate pieces, in an alternative embodiment, retainer 212 and body 102 are manufactured as a single integrated piece. Thus, while a screw thread is shown for attaching retainer 212 to body 102, the exemplary threaded portion can be removed if body 102 and retainer 212 are integrated into a single piece.

Figure 4:
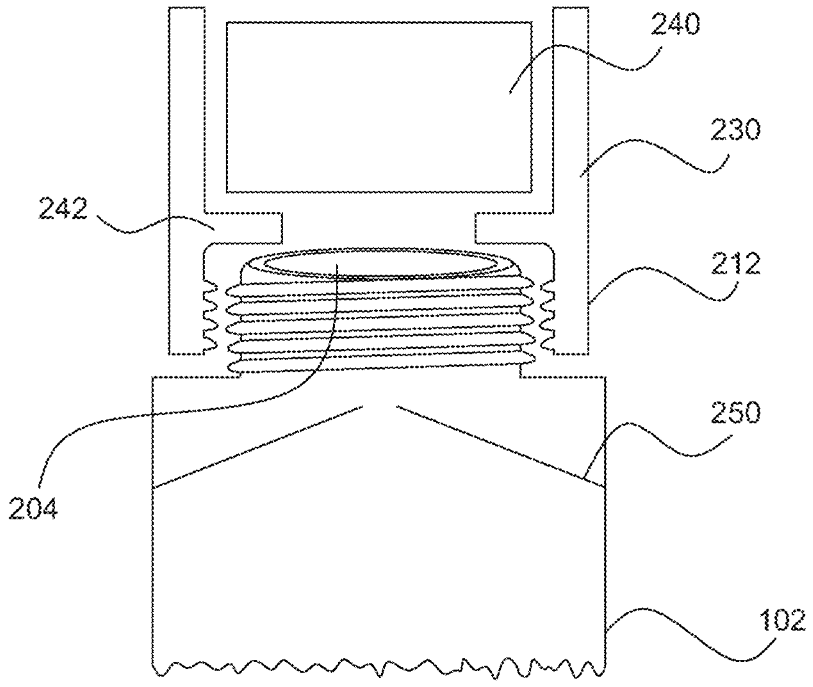
FIG. 4 is a side view of the further removable tip shown in FIG. 3, and a seal for restricting flow of liquid out of a squeezable member in accordance with a further exemplary embodiment of the present invention.

FIG. 4 illustrates a further exemplary embodiment of the present invention which appears similar to the exemplary embodiment shown in FIG. 3; however, seal 250 is included. Seal 250 is similar to the seal that is disclosed in U.S. Pat. No. 5,664,705 which is hereby incorporated by reference in its entirety. As disclosed, seal 250 separates interior portions of hollow interior 104 into two compartments: a dispensing portion above seal 250 which is accessible from the exterior via compressible lip 240, and a storage portion below seal 250. Seal 250 may be affixed to a straight edge portion of sidewalls within hollow interior 104.

When opposing pressure is applied to body 102, prep within hollow interior 104 is pressed against seal 250, causing seal 250 to open. As opposing pressure (or even pressure from one side) against body 102 is increased, seal 250 increases the size of its opening to allow more prep to flow therethrough. Without opposing pressure exerted against body 102, seal 250 remains closed and therefore prep is prevented from flowing past seal 250, through compressible tip 240, and onto skin layer 110.

As disclosed in U.S. Pat. No. 5,664,705, seal 250 may be comprised of a plurality of members that are attached to each other during manufacturing in order to maintain prep within body 102. Score lines may separate the individual valve members. Upon application of pressure while body 102 is squeezed, the valve members open, separating from each other along the score lines. In an exemplary embodiment, score lines may be cut deepest at the apex allowing the valve members to easily separate.

U.S. Pat. No. 5,664,705 discloses that the body is manufactured as a plurality of different members that are bonded (or fused) together during the manufacturing process. This is merely exemplary.

FIG. 4 illustrates retainer 212 and body 102 as two separable components (again threaded members are illustrated) although this is again merely exemplary. In an alternative embodiment, body 102 and retainer 212 may be formed as a single integrated piece. In such an embodiment, the use of threaded members may be omitted.

Figure 5:
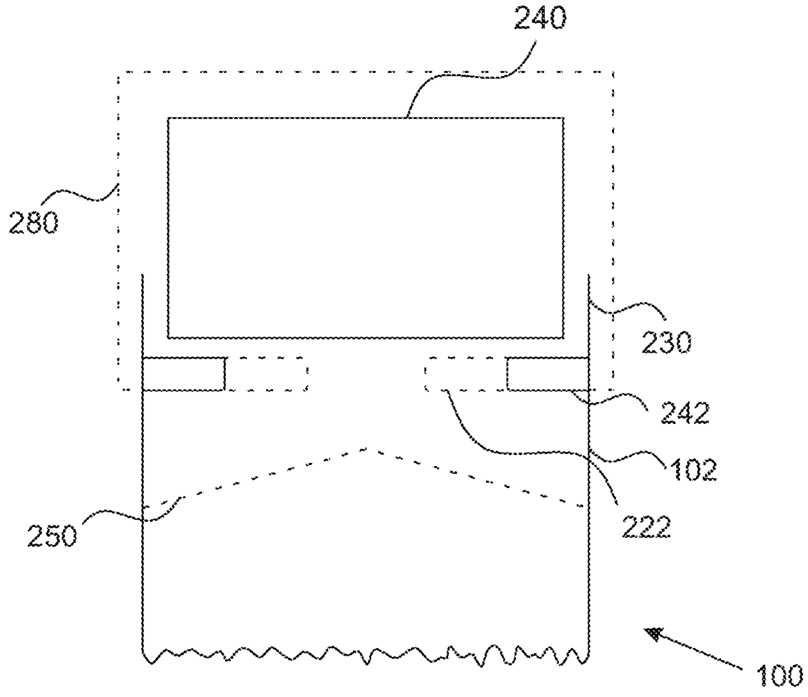
FIG. 5 is a side view of the further removable tip shown in FIG. 3, which is not removable, in accordance with further exemplary embodiments of the present invention.

FIG. 5 illustrates an exemplary embodiment in which squeezable member 100 is supplied as a single integrated item, and as previously described above with regard to alternative exemplary embodiments. In the exemplary embodiment shown in FIG. 5, sidewalls 230 merely extend from body 102 and compressible tip 240 (formed from a sponge-like material, for example) is included. FIG. 5 illustrates that several structures may be used in order to restrict flow out of squeezable member 100. Exemplary structures to restrict flow include seal 250, restrictive member 202, etc. Thus, as shown in FIG. 5, exemplary protrusions 242 are included extending inwards from the inner wall of body 102, and the use of seal 250 may be optional (although it may also be used in combination with restrictive member 222). As described with regard to previous exemplary embodiments, compressible tip 240 may be a friction hold, and/or it may be glued or stapled into the opening defined by sidewall 230, etc. FIG. 4 also illustrates optional cap 280 that may be placed over compressible tip 240 as another form of maintaining skin prep within squeezable member 100 during transportation, or prior to use with the patient. Cap 280 may be a fixed using friction, tongue and groove, threads, etc.

Figure 6A:
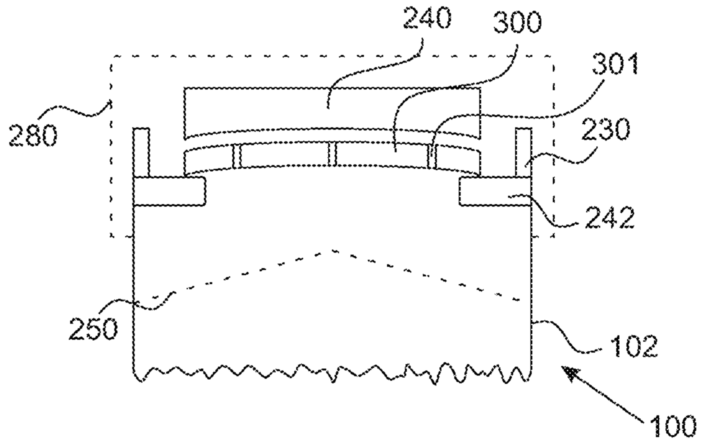
FIG. 6A is a side view of yet another tip, which is not removable, in accordance with a further exemplary embodiment of the present invention.
Figure 6B:
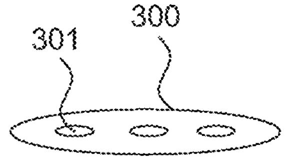
FIG. 6B is a perspective of a disk that may be used for restricting flow in accordance with an exemplary embodiment of the present invention.

FIG. 6A is a cross-sectional side view that illustrates a further exemplary embodiment of the present invention. The structure shown in FIG. 6A is similar to the structure shown in FIG. 5, however, disk 300 has been added. Disk 300 includes openings 301. Disk 300 with disc openings 301 is shown in FIG. 6B. Disk 300 rests on protrusion 242. Disk 300 may be attached to squeezable member 100 within sidewalls 230 by a variety of techniques including chemical bonding, friction, and/or tongue and groove type arrangements. Compressible tip 240 is attached to disk 300. Attachment of compressible tip 242 to disk 300 may be via various different mechanisms including adhesive, friction hold, etc. Optional seal 250 is shown. As prep flows out of body 102, prep flows through openings 301 of disk 300 and through compressible tip 240 before reaching skin layer 110. Optional cap 280 is also shown.

Figure 7:
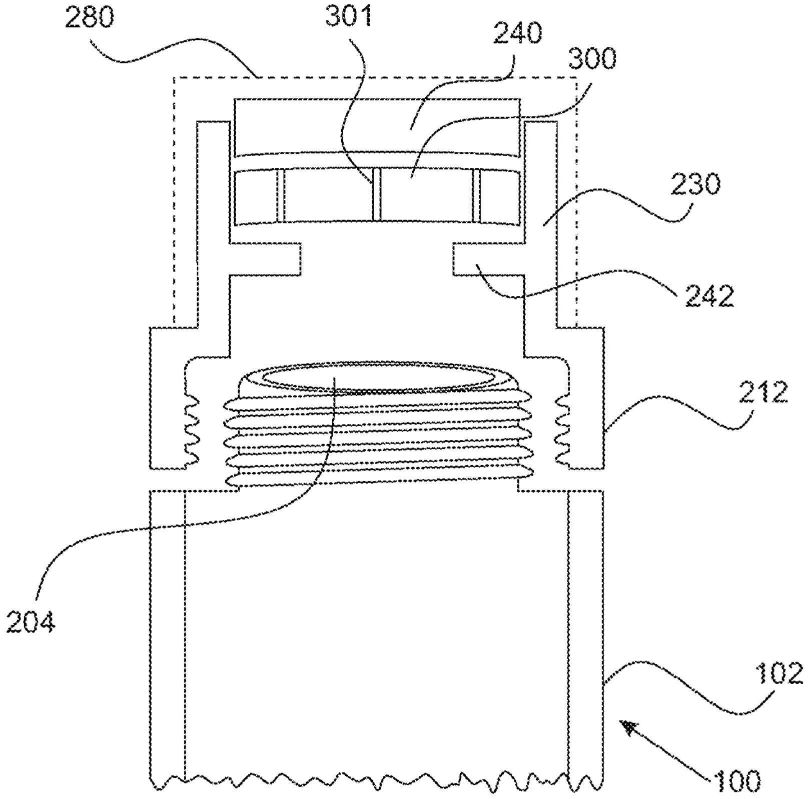
FIG. 7 is a side view of the tip shown in FIG. 6, which is removable, in accordance with a further exemplary embodiment of the present invention.

FIG. 7 is a cross-sectional side view of a further exemplary embodiment of the present invention. The exemplary embodiment shown in FIG. 7 includes disk 300 similarly to the configuration of disk 300 within FIG. 6A. However, while FIG. 6A illustrates squeezable member 100 as a single integrated piece, FIG. 7 illustrates squeezable member 100 as two pieces that may be separated. Thus, in FIG. 7, retainer 212 is included with threaded walls that engage threaded walls at the top of body 102. As described with regard to previous embodiments, while threaded members are shown, this is merely exemplary as other forms of attachment are contemplated. Body opening 204 of body 102 is again illustrated. Thus, in operation, squeezable member 100 may be inverted and may also (or alternatively) have its opposing walls squeezed toward each other so that prep stored therein flows out of body opening 204, passes protrusion 242, passes through openings 301 in disk 300 and through compressible tip 240 before prep reaches skin layer 110.

Figure 8:
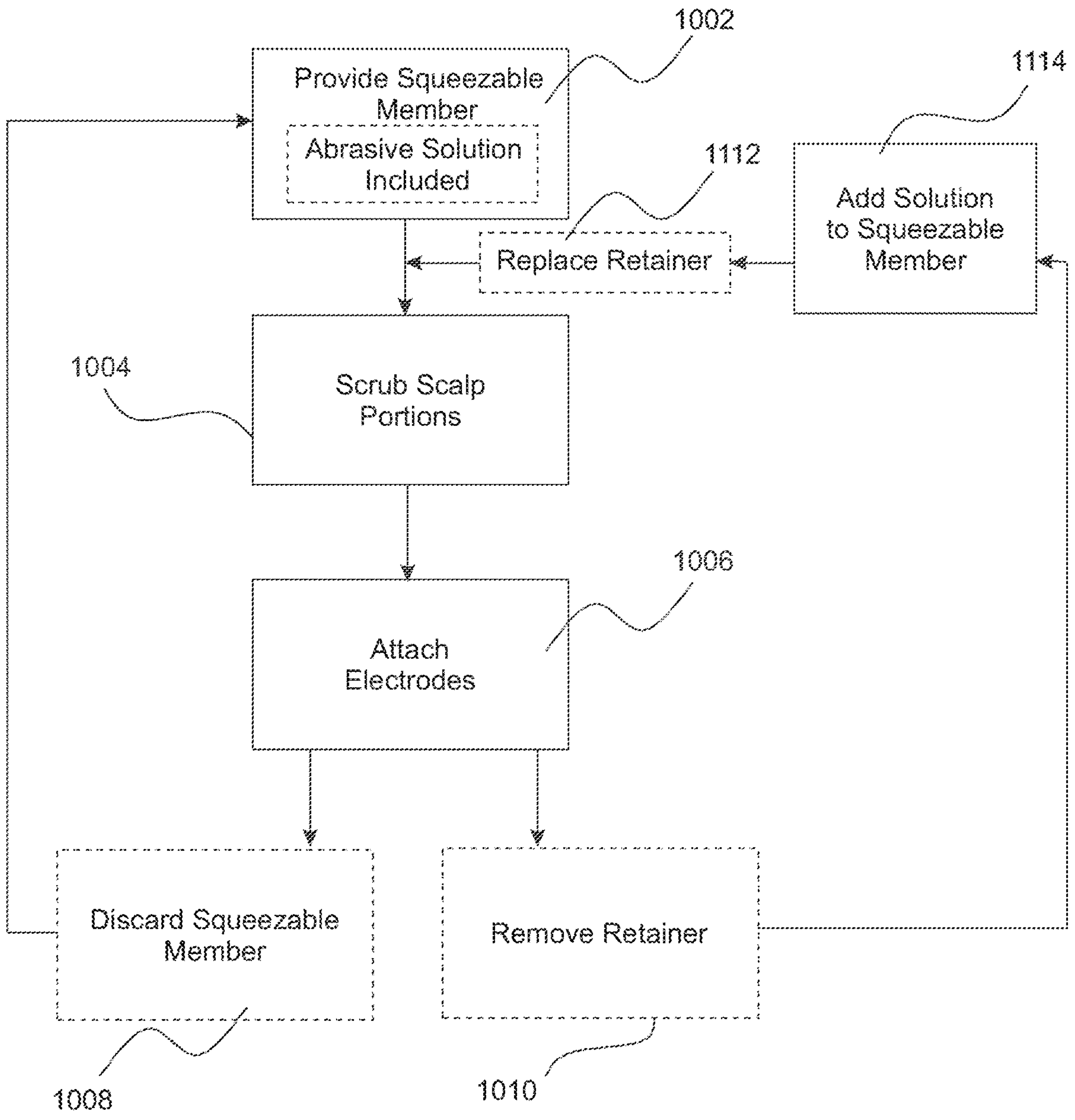
FIG. 8 is a flow chart diagram that illustrates a method for attaching electrodes to a patient in accordance with various exemplary embodiments of the present invention.

FIG. 8 is a flowchart diagram which illustrates operation of an exemplary embodiment of the present invention.

At step 1002, a squeezable member may be provided. For example, squeezable member 100 may be provided. In some exemplary embodiments, abrasive prep is included within the squeezable member. At step 1004, portions of skin layer 110 may be scrubbed. In the preferred embodiment, the portions of skin layer are on the scalp, i.e. located on a person's head. Step 1004 may be accompanied by other steps. One exemplary step that may accompany step 1004 includes the step of inverting the squeezable member so that it is inverted, so it is facing downwards and is in contact with the patient's skin. Furthermore, another exemplary step that may be included is the step of squeezing the squeezable member from opposite sides in order to assist with the dispensing of abrasive prep from the squeezable member. As previously described, squeezing and scrubbing may occur simultaneously, may occur serially (one after the other), or may occur in some combination thereof. At step 1006, electrodes are attached to the patient's skin so that, for example, EEG recording may commence. At step 1008, the squeezable member may be discarded. If the squeezable member is discarded at step 1008, then processing proceeds to step 1002 at which a new squeezable member is provided. Alternatively, if the squeezable member includes a removable retainer, then at step 1010 the removable retainer is removed. At step 1114, solution, namely abrasive prep, is added to the squeezable member. At step 1112, the retainer is replaced onto the squeezable member. Processing then proceeds to step 1004 where skin portions of yet another patient may be scrubbed.

Figure 9:
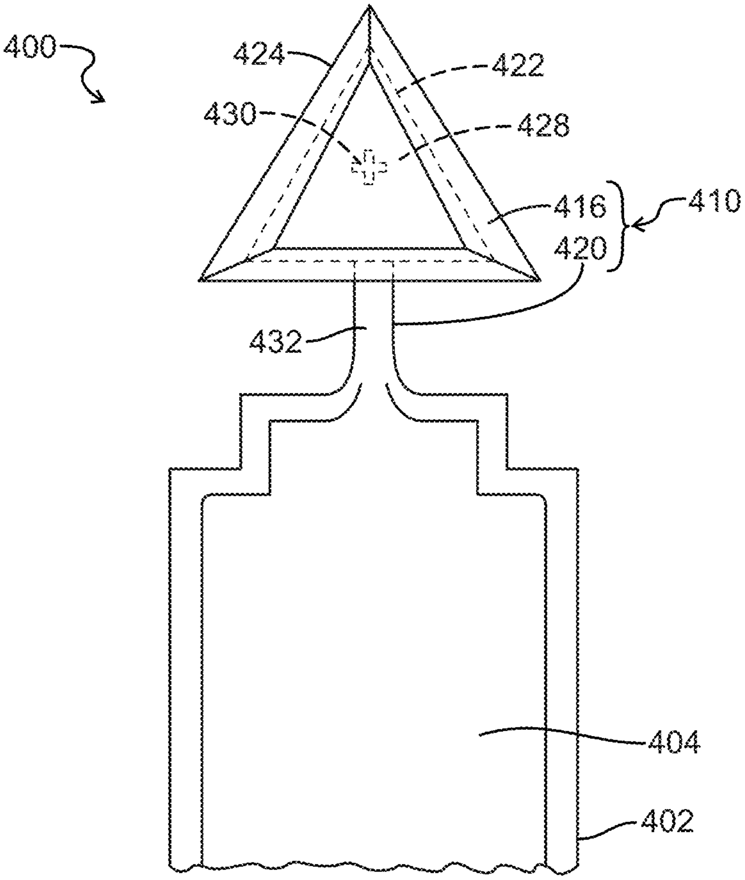
FIG. 9 is a side view of yet another tip in accordance with a further exemplary embodiment of the present invention.

FIG. 9 illustrates a further exemplary embodiment of the squeezable member of the present invention. In FIG. 9, body 402 and applicator 410 of squeezable member 400 are a single integral piece, although this is merely exemplary. In other words, body 402 and applicator 410 may be implemented as two separate pieces. As in earlier embodiments, body 402 has a hollow interior 404. Applicator 410 includes tip 416 and a restrictive member 420, with tip 416 having a triangular shape which may be angled with respect to restrictive member 420. Tip 416 also includes a relatively more rigid interior member 422 and a less rigid exterior member 424. More rigid interior member 422 of tip 416 may be manufactured using various exemplary manufacturing processes including injection molding and blow molding. Front surface 428 of more rigid interior member 422 has a cross-shaped opening 430 which may be other shapes and connects to a hollow interior of more rigid interior member 422. Less rigid exterior member 424 is comprised of a compressible material in order to reduce friction between tip 416 and the skin surface. An exemplary less rigid exterior material layer may be cotton, although other fibers are also contemplated including polyester type fibers. In other embodiments, the exterior member 424 may be formed of a sea sponge material. In addition, the shape of less rigid exterior member 424 in the exemplary embodiment is similar or corresponds to the shape of the interior member 422, which structure assists a technician in applying pressure on to the patient's head while grasping the applicator and contacting the tip 416 with the patient's head with any part of the exterior surface and at any angle with good scrubbing results. Using the applicator 410 greatly improves the efficiency of the skin cleaning process, while also improving patient safety since the applicator 410 is formed of materials that will not break as a result of manual forces exerted on the applicator 410 during skin cleaning. Restrictive member 420 includes restrictive opening 432 through which abrasive prep flows from body 402 into interior member 422 of tip 416. Restrictive opening 432 restricts the rate at which abrasive prep flows into tip 416 and out of opening 430 towards the skin surface.

While several embodiments described above include structure for opening and resealing squeezable member 100, in several embodiments squeezable member 100 is supplied with prep already included therein and with a resealable opening for refilling squeezable member 100 after the prep has exited.

In the aforementioned description, numerous details are set forth. It will be apparent. however, to one skilled in the art, that the disclosure may be practiced without these specific details. In some instances, well-known structures and devices are shown in block diagram form, rather than in detail, in order to avoid obscuring the disclosure.

Whereas many alterations and modifications of the disclosure will no doubt become apparent to a person of ordinary skill in the art after having read the foregoing description, it is to be understood that any particular implementation shown and described by way of illustration is in no way intended to be considered limiting. Therefore, references to details of various implementations are not intended to limit the scope of the claims, which in themselves recite only those features regarded as the disclosure.

ITEM NUMBERS 100 squeezable member
102 body
104 hollow interior
106 restrictive member
107 bottom
108 tip
109 sidewalls
110 skin
202 neck
204 body opening
210 applicator

212 retainer
214 restrictive member
216 rounded tip
218 cover
220 restrictive opening
222 restrictive member
230 sidewall
240 compressible tip
242 protrusion
250 seal
280 cap
300 disk
301 disk opening
410 applicator
416 tip
420 restrictive member
422 interior member
424 exterior member
428 front surface
430 cross-shaped opening
432 restrictive opening

What is claimed is:

1. A method for preparing the skin of a patient's scalp for attaching electrodes to the scalp, said method comprising the steps of:

providing a squeezable member comprising a body, an applicator, and a skin abrasive prep;

said body having a hollow interior chamber in which said skin abrasive prep is located, said hollow interior chamber having a cross-sectional area;

said applicator including a retainer and a tip, said retainer being releasably secured to said body by either a threaded screw connection, a friction hold connection, or a tongue and groove connection;

said tip being configured to enable said skin abrasive prep to flow therethrough from said hollow interior chamber of said body via a restrictive member interposed between said tip and said hollow interior chamber;

said tip including an interior member having one or more openings therein and a hollow interior, and a compressible exterior member applied over the interior member and the one or more openings in the interior member, wherein said interior member is relatively more rigid than the compressible exterior member, and said compressible exterior member and interior member having similar, corresponding shapes;

said restrictive member including an opening having a cross-sectional area which is less than said cross sectional area of said hollow interior chamber;

said body being configured to be squeezed in a direction to cause said skin abrasive prep to flow from said hollow interior chamber through said opening of said restrictive member into said hollow interior of said interior member of said tip and then passing out of said interior member through said one or more openings in the interior member to said compressible exterior member, and then passing through said compressible exterior member out of said tip;

squeezing said squeezable member in said direction to cause said skin abrasive prep to flow from said hollow interior chamber through said opening of said restrictive member into said hollow interior of said interior member of said tip and then through said one or more openings in the interior member to said compressible exterior member, then through said compressible exterior member out of said tip;

bringing said less rigid compressible exterior member of said tip of said applicator into engagement with portions of skin of said patient's scalp and scrubbing said portions of skin of said patient's scalp using a back and forth rubbing motion with said abrasive prep exiting from said tip to produce a scrubbed portion of the patient's scalp, said interior member having a rigidity required for an adequate manual pressure to be applied against the patient's scalp with the tip to repeatedly scrub said portions of the patient's scalp without breaking;

removing said less rigid compressible exterior member of said tip of said applicator from engagement with said scrubbed portions of the patient's scalp; and thereafter attaching electrodes to scrubbed portions of the patient's scalp.

2. The method of attaching electrodes according to claim 1, wherein said skin abrasive prep is introduced into said hollow interior by detaching said applicator from said body, inserting said skin abrasive prep into said hollow interior chamber, and attaching said applicator to said body, wherein said applicator that is detached and said applicator that is reattached is one of a) a same applicator and b) respectively different applicators.

3. The method according to claim 2, wherein said squeezable member is supplied with said respectively different applicators.

4. The method according to claim 1, wherein said compressible exterior member is comprised of cotton.

5. The method according to claim 1, wherein said restrictive member is a seal with an opening of variable size that changes responsive to the amount of squeezing of said squeezable member with said skin abrasive prep therein.

6. The method according to claim 1, wherein said squeezable member is supplied with said skin abrasive prep therein and without a resealable opening for refilling said squeezable member after said skin abrasive prep has exited.

7. The method according to claim 1, wherein while scrubbing said portion of skin of said patient's scalp, pressure is applied to said portions of skin of said patient's scalp in a direction orthogonal to said direction in which said squeezable member is squeezed.

8. The method according to claim 1, wherein said interior member of the tip is rigid, and said exterior member of the tip is a compressible member.

9. The method according to claim 1, wherein said exterior member of the tip comprises a sponge-like material.

10. The method according to claim 1, wherein the exterior member of the tip comprises a textile or fabric.

11. The method according to claim 1, wherein said body comprises a sidewall and wherein said restrictive member comprises a plurality of restrictive members extending radially inward with respect to said body.

12. The method according to claim 1, wherein said squeezable member additionally comprises a cap being releasably secured over said tip by either a threaded screw connection, a friction hold connection, or a tongue and groove connection, and removing the cap from over the tip prior to the step of squeezing said squeezable member to cause said skin abrasive prep to flow from said hollow interior chamber out of said tip.

13. The method according to claim 1, wherein the compressible exterior member of the tip comprises a vegetal cellulose material.

14. The method according to claim 1, wherein the compressible exterior member of the tip has an outer surface shape which is that same as an outer surface shape of the interior member.

15. The method according to claim 14 wherein the tip further comprises a front surface which is angled with respect to the restrictive member to be easily brought into engagement with said portions of skin of said patient's scalp for scrubbing said portions of skin of said patient's scalp, and the one or more openings in the interior member of the tip are in said front surface.

16. The method according to claim 15 wherein said front surface of the tip has a triangular shape.

17. The method according to claim 1 wherein after the step of removing said less rigid compressible exterior member of said tip of said applicator from engagement with said scrubbed portions of the patient's scalp, and prior to the step of attaching electrodes to scrubbed portions of the patient's scalp, the further step of;

applying a conductive paste to a skin contact area of the electrodes to increase adherence of the electrodes to the scrubbed portions of the patient's scalp and to reduce contact impedance at an interface between the electrodes and skin of the scrubbed portions of the patient's scalp.

18. The method according to claim 17 wherein prior to the step of applying a conductive paste to a skin contact area of the electrodes, the further step of:

removing excess skin abrasive prep from the scrubbed portions of the patient's scalp.

* * * * *